United States Patent [19]

Witte et al.

[11] 4,258,058
[45] Mar. 24, 1981

[54] PHENOXYALKYLCARBOXYLIC ACID COMPOUNDS AND THROMBOCYTE-AGGREGATION INHIBITION

[75] Inventors: Ernst-Christian Witte, Mannheim; Hans P. Wolff, Hirschberg-Grossachsen; Max Thiel, Mannheim; Karlheinz Stegmeier, Schriesheim; Egon Roesch, Mannheim, all of Fed. Rep. of Germany

[73] Assignee: Boehringer Mannheim GmbH, Mannheim, Fed. Rep. of Germany

[21] Appl. No.: 15,536

[22] Filed: Feb. 26, 1979

[30] Foreign Application Priority Data

Mar. 4, 1978 [DE] Fed. Rep. of Germany ....... 2809377

[51] Int. Cl.³ ................. C07C 143/78; A61K 31/195; A61K 31/24
[52] U.S. Cl. ............................. 424/309; 260/326 A; 260/465 E; 564/84; 564/89; 564/91; 424/249; 424/319; 424/322; 544/391; 560/10; 560/12; 562/427; 562/430; 564/99
[58] Field of Search .................... 560/10, 12; 562/430, 562/427; 424/309, 319

[56] References Cited

U.S. PATENT DOCUMENTS

| 3,364,249 | 1/1968 | Bolhofer | 562/430 |
| 3,402,198 | 9/1968 | Bolhofer | 560/12 |
| 3,549,689 | 12/1970 | Frey | 560/12 |
| 3,629,320 | 12/1971 | Wasley | 560/12 |
| 3,652,646 | 3/1972 | Leigh | 562/430 |
| 3,720,709 | 3/1973 | Sprague | 560/12 |
| 4,112,236 | 9/1978 | Bicking | 560/12 |

*Primary Examiner*—Natalie Trousof
*Assistant Examiner*—Michael Shippen
*Attorney, Agent, or Firm*—Sprung, Felfe, Horn, Lynch & Kramer

[57] ABSTRACT

Phenoxyalkylcarboxylic acid compounds of the formula

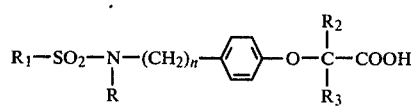

wherein
R is hydrogen or lower alkyl
$R_1$ is alkyl or aryl, aralkyl or aralkenyl radical, the aryl moiety of which can be substituted one or more times by halogen, hydroxyl, trifluoromethyl or lower alkyl, alkoxy or acyl
$R_2$ and $R_3$ are individually selected from hydrogen or lower alkyl, and
n is 0, 1, 2 or 3 and the physiologically acceptable salts, esters and amides thereof; are outstandingly effective in inhibiting thrombocyte aggregation.

20 Claims, No Drawings

PHENOXYALKYLCARBOXYLIC ACID COMPOUNDS AND THROMBOCYTE-AGGREGATION INHIBITION

The present invention relates to phenoxyalkylcarboxylic acid compounds, to pharmaceutical compositions containing them, and to methods for inhibiting thrombocyte aggregation and for depressing serum lipids, utilizing such compounds.

German Patent Specification Nos. 2,149,070, 2,405,622 and 2,541,342 describe lipid-depressing phenoxyalkylcarboxylic acid derivatives, the phenyl radical of which is substituted by various acylaminoalkyl radicals.

We have now, surprisingly, found that analogous phenoxyalkylcarboxylic acid derivatives, the phenyl radical of which is substituted by a sulphonylamino or sulphonylaminoalkyl radical, also display a significant lipid-depressing action but essentially exhibit an outstanding inhibiting action of thrombocyte aggregation.

Thus, the present invention provides phenoxyalkylcarboxylic acid compounds of the formula:

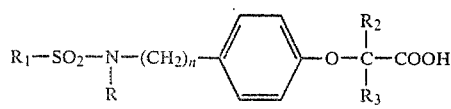

wherein
R is hydrogen or lower alkyl
$R_1$ is alkyl or aryl, aralkyl or aralkenyl radical, the aryl moiety of which can be substituted one or more times by halogen, hydroxyl, trifluoromethyl or lower alkyl, alkoxy or acyl
$R_2$ and $R_3$, which can be the same or different, are hydrogen or lower alkyl and
n is 0, 1, 2 or 3;
as well as the physiologically acceptable salts, esters and amides thereof.

The new compounds of general formula (I) and their physiologically acceptable salts, as well as their esters and amides, display, in vitro, an outstanding inhibition of induced thrombocyte aggregation. Furthermore, they prove to be effective lipid sinking agents.

The alkyl radicals $R_1$ have straight or branched chains containing up to 16 carbon atoms, preferred alkyl radicals including methyl, ethyl, octyl and hexadecyl.

The aralkyl radicals are those in which the alkyl moiety contains up to 5 carbon atoms, which can be straight-chained or branched, the phenethyl and 4-chlorophenethyl radicals being preferred.

The aralkenyl radicals are those in which the alkenyl moiety contains 2 or 3 carbo atoms, the styryl and 4-chlorostyryl radicals being preferred.

The aryl radicals are aromatic hydrocarbon radicals containing 6 to 14 carbon atoms, the phenyl, biphenyl, naphthyl and fluorenyl radicals being preferred. These aryl radicals can be substituted one or more times in all possible positions, the substituents thereby being halogen atoms, hydroxyl groups and alkyl, alkoxy, trifluoromethyl and acyl radicals.

The halogen atoms are preferably fluorine, chlorine or bromine atoms.

The alkyl and alkoxy radicals are, in all cases, radicals containing up to 5 carbon atoms, which can be straight-chained or branched. The straight-chained alkyl radical is preferably methyl, the branched alkyl radical is preferably tert.-butyl and the alkoxy radical is preferably methoxy. The preferred acyl radical is acetyl.

The lower alkyl radicals R, $R_2$ and $R_3$ can be straight-chained or branched and contain up to 6 and preferably up to 4 carbon atoms.

The esters derived from carboxylic acids of general formula (I) contain, as alcohol component, a lower monohydroxy alcohol, of which methanol, ethanol and propanol are preferred, as well as polyhydroxy alcohols, for examle, glycol or glycerol, or alcohols with other functional groups, for example ethanolamine or glycol ethers.

The amides according to the present invention derived from carboxylic acids of general formula (I) can contain, as amine component, for example, ammonia, p-aminobenzoic acid, β-alanine, ethanolamine and 2-aminopropanol, as well as the amino acid of the formula:-

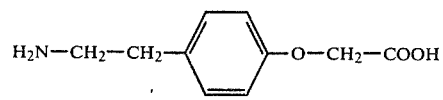

the hitherto mentioned ones being preferred. However, alkylamines, for example isopropylamine and tert.-butylamine, dialkylamines, for example diethylamine, as well as cyclic amines, for example morpholine and 4-alkyl- or -aralkyl- or -arylpiperazines, for example 4-methylpiperazine, 4-(4-chlorobenzyl)-piperazine and 4-(3-methoxyphenyl)-piperazine can also be used.

The above-given definitions of the compounds according to the present invention are also to include all possible stereoisomers, as well as mixtures thereof.

The new compounds of general formula (I) according to the present invention can be prepared by reacting an amine of the general formula:

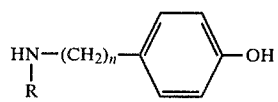

in which R has the same meaning as above, possibly with intermediate protection of the amino or hydroxyl group, in known manner and in any order with a sulphonic acid of the general formula:

in which $R_1$ has the same meaning as above, or with a derivative thereof, and with a compound of the general formula:

wherein $R_2$ and $R_3$ have the same meanings as above, X is a reactive group and Y is a -COOR$_4$ group ($R_4$ being a hydrogen atom or a lower alkyl radical) or an acid amide group. However, Y can also represent a residue which, after condensation has taken place, can be converted into an acid amide group or into a -COOR$_4$ group, whereupon, if desired, a particular substituent $R_4$ is subsequently converted, after the condensation, in known manner, into a different substituent $R_4$ and, if desired, a compound obtained is converted into a pharmacologically acceptable salt.

When $R_2$ and $R_3$ signify lower alkyl radicals, the phenols of general formula (II) or the reaction products thereof with a sulphonic acid of general formula (III) can also be reacted with a mixture of an aliphatic ketone, chloroform and an alkali metal hydroxide. This process variant is preferably used for the preparation of isobutyric acid derivatives, acetone thereby being used as the ketone (cf. in this regard Gazz. Chim. ital., 77, 431/1947).

The process according to the present invention is preferably carried out in two steps. The condensation of a compound of general formula (II) with a sulphonic acid of general formula (III) or with a derivative thereof, on the one hand, and with a compound of general formula (IV), on the other hand, is preferably carried out in such a manner that first one of the two reactive groups of the compound (II) is blocked with a protecting group which can easily be split off, the compound obtained is reacted with a sulphonic acid (III) or with a derivative thereof or with a compound of general formula (IV), the protecting group is again split off and the reactive intermediate thus obtained is subsequently reacted with the compound of general formula (IV) or (III) which has not already been used. A synthesis route is preferred in which a compound (II) protected on the amino group is first reacted with a compound (IV). After removing the protecting group, the reaction with a sulphonic acid (III) or with a derivative thereof is then carried out.

Instead of the free amines (II), it is also possible to employ the salts thereof.

A further possibility for the preparation of compounds of general formula (I), of their salts, as well as of their esters and amides, consists in reacting a sulphonamide of the general formula:

(V)

wherein R and $R_1$ have the same meanings as above, with a compound of the general formula:

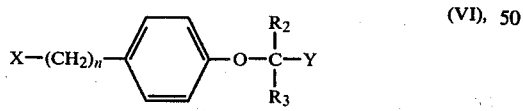

(VI), wherein $R_2$, $R_3$, X and n have the same meanings as above, to give a compound of the general formula:

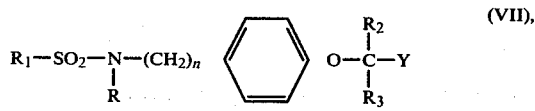

(VII), in which R, $R_1$, $R_2$, $R_3$, Y and n have the same meanings as above.

A third possibility of synthesis consists in a transacylation: if a free sulphonic acid (III) is reacted with a compound of the general formula:

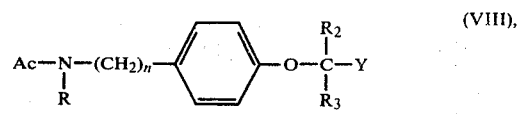

(VIII), wherein n, R, $R_2$, $R_3$ and Y have the same meanings as above and Ac is a readily exchangeable acyl radical, in an appropriate solvent, then there are again obtained sulphonamides of general formula (VII).

The reactive derivatives of the sulphonic acids (III) are preferably the halides, as well as the esters. The reaction of a sulphonic acid halide with a compound of general formula (II) is preferably carried out with the addition of an acid-binding agent, for example, an alkali metal acetate, sodium bicarbonate, sodium carbonate, sodium phosphate, calcium oxide, calcium carbonate or magnesium carbonate. This function can, however, be undertaken by an organic base, for example pyridine or triethylamine, using, as inert solvent, for example, diethyl ether, benzene, methylene chloride, dioxan or an excess of the tertiary amine. When using an inorganic acid-binding agent, the reaction medium used can be, for example, water, aqueous ethanol or aqueous dioxan.

For the reaction of a compound (II) with a compound (IV), it has proved to be advantageous first to convert the amino group of the compound (II) into a protected group, for example a phthalimido group, which, after the reaction, can easily be removed again in known manner with, for example, hydroxylamine. However, other groups known from peptide chemistry can also be used for protecting the amino group and then removed again after the reaction. It is preferred to block the amino group with an acyl radical, for example a formyl or acetyl radical, which, after the reaction, can easily be removed again with a strong base, for example sodium hydroxide or potassium hydroxide, but also with an aqueous mineral acid, for example hydrochloric acid.

As reactive compounds (IV), those are especially preferred in which X represents an anion of a strong acid, for example of a hydrohalic or sulphonic acid. The reaction can be further promoted by converting the phenolic hydroxyl group of the compound (II) into a phenolate, for example by reaction with a sodium alcoholate. The reaction of the two components is carried out in a solvent, for example toluene, xylene, methyl ethyl ketone or dimethylformamide, preferably at an elevated temperature.

For the alkylation of the sulphonic acid amides (V), it is preferable to use compounds (VI), wherein X is an arylsulphonyloxy radical, X more preferably being a toluene-sulphonyloxy radical. Thus, as alkylation agents, there are preferably employed alkyl arylsulphonates, a method for the use of which for sulphonic acid amides, is described by Klamann et al., in Monatshefte für Chemie, 83, 871/1952. The reaction takes place in an alkaline medium, a hot, concentrated aqueous solution of sodium carbonate being the preferred reaction medium.

The transacylation reaction between a free sulphonic acid (III) and an acylamine (VIII) is preferably carried out with the use of equimolar amounts of the two reaction components in a polar solvent, examples of such polar solvents including alcohols and especially ethanol and methanol. The reaction is preferably carried out at the boiling temperature of the solvent. An example of a readily exchangeable acyl radical is the acetyl radical.

As substituents Y of general formula (IV) which can be converted into the —COOR$_4$ group, there may be mentioned, for example, the nitrile, carbaldehyde, hydroxymethyl, aminomethyl and formyl groups.

A possible subsequent N-alkylation of a compound of general formula (I), in which R is a hydrogen atom, can be carried out in known manner, preferably by reacting a compound in which R is a hydrogen atom with an alkyl halide or a dialkyl sulphate in the presence of an acid-binding agent, for example sodium hydroxide.

A conversion of a substituent R$_4$ into a different substituent R$_4$ can be carried out after the condensation takes place, for example, by saponification of the carboxylic acid esters (R$_4$=alkyl) to give the corresponding carboxylic acids (R$_4$=hydrogen) with a mineral acid or an alkali metal hydroxide in a polar solvent, for example water, methanol, ethanol, dioxan or acetone. Saponification is advantageously carried out with a strong base, such as sodium or potassium hydroxide, in a mixture of methanol and water at ambient temperature or at a moderately elevated temperature. On the other hand, however, the carboxylic acids can also be esterified in the usual manner or esters with a particular residue R$_4$ can be transesterified to give an ester with a different residue R$_4$. The esterification of the carboxylic acids is preferably carried out in the presence of an acidic catalyst, for example, hydrogen chloride, sulphuric acid, p-toluenesulphonic acid or a strongly acidic ion exchange resin. Transesterifications, on the other hand, require the addition of a small amount of a basic substance, for example of an alkali metal or alkaline earth metal hydroxide or of an alkali metal alcoholate. For the esterification of the carboxylic acids or for the transesterification, there can, in principle, be used all alcohols. It is preferable to use lower monohydroxy alcohols, for example methanol, ethanol or propanol, as well as polyhydroxy alcohols, for example glycol, or alcohols with other functional groups, for example ethanolamine or glycol ethers.

The amides according to the present invention derived from the carboxylic acids of general formula (I) are preferably prepared by known methods from the carboxylic acids or their reactive derivatives, for example carboxylic acid halides, esters, azides, anhydrides or mixed anhydrides, by reaction with amines. The amino component can be, for example, ammonia, an alkylamine or a dialkylamine, as well as an aminoalcohol, for example ethanolamine or B 2-aminopropanol, and also an amino acid, for example p-aminobenzoic acid, β-alanine or the like. Other useful amine components include the alkyl-, aralkyl- and arylpiperazines.

For the preparation of salts with pharmacologically acceptable organic or inorganic bases, for example, sodium hydroxide, potassium hydroxide, calcium hydroxide, ammonium hydroxide, methylglucamine, morpholine or ethanolamine, the carboxylic acids can be reacted with the appropriate bases. Mixtures of the carboxylic acids with an appropriate alkali metal carbonate or bicarbonate can also be used.

For the preparation of pharmaceuticals, the compounds according to the present invention are mixed in the usual way with appropriate pharmaceuticl carrier materials and aroma, flavoring and coloring materials and formed, for example, into tablets or dragees or, with the addition of appropriate adjuvants, suspended or dissolved in water or in an oil, for example olive oil.

The new compounds according to the present invention can be administered orally or parenterally in liquid or solid form. As injection medium, it is preferred to use water which contains the stabilizing agents, solubilizing agents and/or buffers usual in the case of injection solutions. Additives of this type include, for example, tartrate and borate buffers, ethanol, dimethyl sulphoxide, complex-forming agents (such as ethylenediamine-tetraacetic acid), high molecular weight polymers (such as liquid polyethylene oxide) for viscosity regulation and polyethylene derivatives of sorbitol anhydrides.

Solid carrier materials can be, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and sweetening agents.

The following Examples, which are given for the purpose of illustrating the present invention, describe some of the numerous process variants which can be used for the synthesis of the new compounds according to the present invention:

EXAMPLE 1

4-[2-(Benzenesulphonylamino)-ethyl]-phenoxyacetic acid.

Process I.

(a) A mixture of 240 g. (1.34 mol) N-acetyltyramine, 370 g. (2.68 mol) anhydrous powdered potassium carbonate and 2.5 liters butan-2-one are heated to reflux temperature for 2 hours, while stirring. 266 g. (1.47 mol) Ethyl bromoacetate and 1.5 g. potassium iodide are then added thereto and the reaction mixture again heated to reflux temperature. After about 6 hours, the reaction is complete. The reaction mixture is then filtered, the filter cake is washed with acetone and the combined filtrates are evaporated in a vacuum. The residue is taken up in 1.75 liters methylene chloride. The methylene chloride phase is washed three times with 300 ml. amounts of 0.5 N aqueous sodium hydroxide solution and once with 300 ml. water, dried with anhydrous sodium sulphate and then evaporated in a vacuum. There are thus obtained 321 g. (98% of theory) ethyl 4-(2-acetylaminoethyl)-phenoxyacetate; m.p. 85° C.

Using the same synthesis route, ethyl 4-(2-acetylaminoethyl)-phenoxyacetate can also be prepared from N-acetyltyramine and ethyl chloroacetate. The reaction time is 9 hours and the yield is quantitative; m.p. 83°–84.5° C.

(b) A mixture of 489.6 g. (1.845 mol) ethyl 4-(2-acetylaminoethyl)-phenoxyacetate and 2.77 liters (5.55 mol) 2 N hydrochloric acid is stirred for 8 hours at reflux temperature, then cooled and the solution adjusted to pH 6 with about 460 ml. 10 N aqueous sodium hydroxide solution. After cooling in an ice-bath, the reaction mixture is filtered with suction. The filter cake is treated twice with 250 ml. amounts of water, sharply filtered off with suction and dried in a vacuum at 50° C. There are obtained 299.5 g. (83% of theory) 4-(2-aminoethyl)-phenoxyacetic acid; m.p. 292° C. (decomp.).

(c) 280 g. (1.435 mol) 4-(2-Aminoethyl)-phenoxyacetic acid are suspended in a solution of 2.85 liters water and 436 g. (3.157 mol) anhydrous potassium carbonate and, while stirring, 266 g. (1.507 mol) benzenesulphochloride allowed to run in in the course of 45 minutes. The reaction mixture is subsequently stirred for 2.5 hours at 80° C. After cooling, 1 liter ethyl acetate is added to the reaction mixture and this then acidified, while stirring, with 800 ml. 6 N hydrochloric acid. The organic phase is then separated off and the aqueous phase is extracted with 1 liter ethyl acetate. The organic phases are combined and extracted with an amount of saturated aqueous sodium bicarbonate solution which is sufficient for salt formation. The aqueous phase is filtered and, while stirring, adjusted to pH 1 with 6 N hydrochloric acid, the product thereby precipitating out in the form of a brownish granulate. This is filtered off with suction, washed with some water and dried in the air. The substance is now dissolved in about 3 liters warm diethyl ether, a greasy, dark brown residue thereby remaining undissolved. The clear ethereal phase is decanted off and evaporated. There are obtained 312 g. (65% of theory) colorless 4-[2-(benzenesulphonylamino)ethyl]-phenoxyacetic acid; m.p. 117°–118° C. After recrystallisation from toluene, the product melts at 119°–120° C.

For the preparation of the N-acetyltyramine used as starting material, there can be used the following methods:

1. While stirring, 64.0 g. (0.466 mol) tyramine are mixed with 200 ml. acetic anhydride, whereby, with spontaneous heating, a clear solution results. This solution is seeded with a few crystals of N-acetyltyramine, whereafter crystallization takes place immediately. The reaction mixture is rapidly cooled, filtered with suction, washed with diethyl ether and water and dried. There are obtained 59 g. (71% of theory) N-acetyltyramine; m.p. 124°–126° C. By evaporating the mother liquor, dissolving the residue in dilute aqueous sodium hydroxide solution, filtering and acidifying the filtrate, there are obtained a further 5.5 g. (6% of theory) of product; m.p. 122°–124° C. After recrystallization from ethyl acetate, N-acetyltyramine melts at 129°–131° C.

2. 65.8 g. (0.84 mol) Acetyl chloride are added dropwise to a solution of 54.9 g. (0.4 mol) tyramine and 200 ml. pyridine, while stirring at 30°–35° C. The reaction mixture is subsequently heated for 15 minutes on a boiling water-bath, then cooled and poured into an ice-water mixture. By the addition of concentrated hydrochloric acid, it is rendered distinctly acidic and subsequently extracted with chloroform. The chloroform phase is washed with water, dried over anhydrous calcium chloride and then evaporated. There are obtained 88.5 g. (quantitative yield) of a residue of diacetyltyramine; m.p. 99°–100° C., after recrystallization from benzene. The diacetyltyramine is now dissolved in 500 ml. methanol. 800 ml. (0.8 mol) 1 N aqueous potassium hydroxide solution are added dropwise thereto, the temperature thereby increasing to about 30° C., and then maintained for 2 hours at an internal temperature of 50° C. The reaction mixture is then cooled, rendered weakly acidic with concentrated hydrochloric acid and the methanol evaporated off in a vacuum. The product which crystallizes out is filtered off with suction, thoroughly washed with water and then dried. The yield of N-acetyltyramine is 58.3 g. (81% of theory); m.p. 131° C., after recrystallization from ethyl acetate.

Process II 19.3 g. (0.11 mol) Benzenesulphonyl chloride are added dropwise to a mixture of 15.0 g. (0.11 mol) tyramine, 18.0 g. (0.22 mol) anhydrous sodium acetate and 250 ml. 97% ethanol and subsequently heated to reflux temperature for 2 hours. The reaction mixture is then freed from ethanol in a vacuum, the residue is mixed with water and the aqueous phase acidified with 2 N hydrochloric acid. The precipitated product is taken up in diethyl ether, extracted several times with diethyl ether and the combined ethereal phases dried with anhydrous sodium sulphate. The diethyl ether is then distilled off and the residue triturated with ligroin. For purification, the product is dissolved in 2 N aqueous sodium hydroxide solution, the solution is treated with active charcoal and the phenolic compound then precipitated out again with dilute hydrochloric acid. After washing with water and drying, there are obtained 23.5 g. (77% of theory) 4-[2-(benzenesulphonylamino)-ethyl]-phenol; m.p. 131° C.

11.9 g. (71.5 mMol) Ethyl bromoacetate are added dropwise, while stirring at the boiling temperature, to a mixture of 18.0 g. (65 mMol) 4-[2-(benzenesulphonylamino)-ethyl]-phenol, 8.95 g. (65 mMol) anhydrous powdered potassium carbonate and 250 ml. ethanol and the reaction mixture then further kept for 2.5 hours at reflux temperature. The reaction mixture is then evaporated in a vacuum, the residue is extracted several times with diethyl ether and the ethereal extracts are evaporated. The product remaining behind is recrystallized from a mixture of ethyl acetate and ligroin. There are obtained 9.8 g. (42% of theory) ethyl 4-[2-(benzenesulphonylamino)-ethyl]-phenoxyacetate; m.p. 68°–70° C.

A mixture of 22.1 g. (61 mMol) ethyl 4-[2-(benzenesulphonylamino)-ethyl]-phenoxyacetate, 183 ml. (183 mMol) 1 N aqueous potassium hydroxide solution and 250 ml. methanol is kept for 2 hours at 35° C. It is then acidified with 2 N hydrochloric acid, the methanol is evaporated off and the remaining aqueous phase is extracted several times with methylene chloride. The combined methylene chloride phases are washed with water, dried over anhydrous sodium sulphate and evaporated. The evaporation residue is triturated with ligroin and filtered with suction. There are obtained 17.6 g. (86% of theory) 4-[2-(benzenesulphonylamino)-ethyl]-phenoxyacetic acid; m.p. 116°–118° C.

Process III 13.3 g. (75 mMol) Benzene-sulphochloride are added dropwise, while stirring, over the course of one hour to an ice-cooled solution of 19.5 g. (75 mMol) ethyl 4-(2-aminoethyl)-phenoxyacetate hydrochloride. The cooling bath is then removed and the reaction mixture stirred for 2 hours at ambient temperature. Subsequently, it is poured into ice water and acidified with concentrated hydrochloric acid, whereby an oil separates out which is taken up in diethyl ether. The aqueous phase is further extracted several times with diethyl ether and the combined ethereal phases are dried with anhydrous sodium sulphate and subsequently evaporated. There are obtained 22.3 g. (82% of theory) ethyl 4-[2-(benzenesulphonylamino)-ethyl]-phenoxyacetate; m.p. 76°–77° C.

Saponification of this ethyl ether to give the free 4-[2-(benzenesulphonylamino)-ethyl]-phenoxyacetic acid is carried out in the manner described above.

(a) Isopropyl 4-[2-(benzenesulphonylamino)-ethyl]-phenoxyacetate

A mixture of 7.28 g. (20 mMol) ethyl 4-[2-(benzenesulphonylamino)-ethyl]-phenoxyacetate, 75 ml. isopropanol and about 50 mg. sodium isopropylate is heated for 12 hours at reflux temperature and subsequently the isopropanol is distilled off. The residue is treated with 0.5 N hydrochloric acid and diethyl ether and the ethereal phase is dried and evaporated. The oil which remains behind is triturated with ligroin to give 4.5 g. (67% of theory) isopropyl 4-[2-(benzenesulphonylamino)-ethyl]-phenoxyacetate; m.p. 56°–57° C.

EXAMPLE 2

4-[2-(4-Methoxybenzenesulphonylamino)-ethyl]-phenoxyacetic acid

A mixture of 10.35 g. (50 mMol) 4-methoxybenzenesulphonyl chloride and 50 ml. pyridine is added dropwise at 0°–10° C. in the course of 5 minutes to a solution of 11.2 g. (50 mMol) ethyl 4-(2-aminoethyl)-phenoxyacetate in 125 ml. anhydrous pyridine. The reaction mixture is allowed to warm up to ambient temperature and then kept at 60° C. for 45 minutes. Subsequently, the reaction mixture is evaporated to half its volume in a vacuum, then poured into ice-water and acidified with hydrochloric acid. The precipitated viscous mass is dissolved in toluene and the toluene phase successively extracted with dilute hydrochloric acid, an aqueous solution of sodium bicarbonate and water. After drying over anhydrous calcium chloride, the solution is evaporated in a vacuum and the residue triturated with some diethyl ether, crystallization thereby takes place. The product is filtered off with suction and recrystallized from a very small amount of diethyl ether. There are thus obtained 13.0 g. (66% of theory) ethyl 4-[2-(4-methoxybenzenesulphonylamino)-ethyl]-phenoxyacetate; m.p. 82°–83° C.

In the case of the availability of 4-[2-(4-methoxybenzenesulphonylamino)-ethyl]-phenoxyacetic acid, its ethyl ester can also be synthesized in the following way:

The acid is dissolved in twenty times its quantity by weight of absolute ethanol and the surface of the solution gassed with dry hydrogen chloride, the temperature thereby being maintained at 50° to 60° C., until saturation is achieved. The reaction mixture is then maintained for 30 minutes at 50° to 60° C., subsequently evaporated in a vacuum and the yellowish, initially oily residue obtained recrystallized from diethyl ether. The yield is about 90% of theory.

70 ml. (70 mMol) 1 N Aqueous potassium hydroxide solution is added dropwise to a solution of 11.8 g. (30 mMol) ethyl 4-[2-(4-methoxybenzenesulphonylamino)-ethyl]-phenoxyacetate and 70 ml. ethanol and the reaction mixture then kept for 5 hours at 35° to 40° C. The ethanol is subsequently distilled off in a vacuum and the aqueous phase extracted with diethyl ether. The addition of 35 ml. 2 N hydrochloric acid leads to the precipitation of a colorless material which is filtered off with suction and recrystallized from dilute acetic acid. There are obtained 8.66 g. (79% of theory) 4-[2-(4-methoxybenzenesulphonylamino)-ethyl]-phenoxyacetic acid; m.p. 103° C.

The preparation of the ethyl 4-(2-aminoethyl)-phenoxyacetate or of its hydrochloride required for the reaction can take place in two ways:

A. From 4-(2-aminoethyl)-phenoxyacetic acid and ethanol:

Dry hydrogen chloride gas is passed, while stirring, on to a cooled (5°–10° C.) solution of 67.2 g 4-(2-aminoethyl)-phenoxyacetic acid and 672 ml. anhydrous ethanol until the solution is saturated. After standing overnight, the reaction mixture is evaporated at 30° C. The crystalline residue is then left to dry first in the air and then over potassium hydroxide. There are obtained 85.6 g. (96% of theory) ethyl 4-(2-aminoethyl)-phenoxyacetate hydrochloride which, after recrystallization from isopropanol, melts at 158°–160° C. The free base, which is a viscous oil, condenses very quickly.

B. Via 4-[2-(phthalimido)-ethyl]-phenol:

A mixture of 137.1 g. (1 mol) tyramine, 148.1 g. (1 mol) phthalic anhydride, 13 ml. triethylamine and 2 liters toluene is heated under reflux on a water separator until the theoretical amount of water has separated. The reaction mixture is then allowed to cool and the precipitate obtained filtered off. There are obtained 259 g. (97% of theory) 4-[2-(phthalimido)-ethyl]-phenol; m.p. 223°–226° C. After recrystallization from isopropanol, the compound melts at 228°–230° C.

34.7 g. (0.13 mol) 4-[2-(Phthalimido)-ethyl]-phenol and 35.9 g. (0.26 mol) anhydrous, powdered potassium carbonate are heated under reflux, while stirring, for 2 hours in 300 ml. dry acetone. 31.8 g. (0.19 mol) Ethyl bromoacetate and 0.2 g. potassium iodide are then added thereto and the reaction mixture maintained at reflux temperature for a further 8 hours. The inorganic precipitate is filtered off, washed with acetone and the combined filtrates evaporated in a vacuum. The residue is taken up in chloroform, the solution washed with 0.5 N aqueous sodium hydroxide solution and water, dried and evaporated. The residue is recrystallized from isopropanol. There are obtained 38.8 g. (83% of theory) ethyl 4-[2-(phthalimido)-ethyl]-phenoxyacetate; m.p. 104°–106° C.

35.3 g. (0.1 mol) of this ester are dissolved in 1 liter of boiling ethanol and mixed, while hot, with 7.5 g. (0.15 mol) hydrazine hydrate. The solution is left to stand overnight, acidified with a little concentrated hydrochloric acid and then evaporated. The residue is stirred into 1 liter water, insoluble material is filtered off and the aqueous filtrate is evaporated. With the addition of charcoal, the evaporation residue is recrystallized from isopropanol. There are obtained 17.2 g. (66% of theory) ethyl 4-(2-aminoethyl)-phenoxyacetate hydrochloride; m.p. 157°–160° C.

EXAMPLE 3

4-[2-(4-Fluorobenzenesulphonylamino)-ethyl]-phenoxyacetic acid 16.35 g. (84 mMol) 4-Fluorobenzenesulphonyl chloride are added dropwise at 10° to 15° C. to a mixture of 160 ml. anhydrous pyridine, 11.1 g. (80 mMol) pulverized, anhydrous potassium carbonate and 20.8 g. (80 mMol) ethyl 4-(2-aminoethyl)-phenoxyacetate hydrochloride. The reaction mixture is subsequently stirred for 30 minutes at 20° C. and for 5 minutes at 80° C. and then cooled and poured into ice-water. The solution is acidified with concentrated hydrochloric acid and the precipitated material extracted with methylene chloride. After drying over anhydrous sodium sulphate, the methylene chloride phase is evaporated and the evaporation residue recrystallized from a methanol-water mixture. There are thus obtained 25.5 g. (84% of theory) ethyl 4-[2-(4-fluorobenzenesulphonylamino)-ethyl]-phenoxyacetate; m.p. 75°–78° C.

By hydrolysis of the ethyl ester in a manner analogous to that described in Example 2, there is obtained a yield of 87% of theory of 4-[2-(4-fluorobenzenesulphonylamino)-ethyl]-phenoxyacetic acid; m.p. 206°–208° C.

For the preparation of the sodium salt, 7.46 g. (21.1 mMol) of the acid are suspended in 150 ml. methanol, warmed to about 40° C. and 21.1 ml. 1 N aqueous sodium hydroxide solution added thereto. Thereafter, the solution is evaporated in a vacuum and the residue is triturated with acetone, filtered off with suction and washed with acetone. There are obtained 7.8 g. of the sodium salt; m.p. 260°–270° C. (decomp.).

In an analogous manner, by the reaction of ethyl 4-(2-aminoethyl)-phenoxyacetate hydrochloride with the appropriate sulphonyl chlorides in the presence of pyridine and potassium carbonate, there are obtained:

(a) ethyl 4-[2-(methanesulphonylamino)-ethyl]-phenoxyacetate as a viscous oil;
yield 65% of theory;
IR maxima: 3290 cm$^{-1}$, 1750 cm$^{-1}$; 1608 cm$^{-1}$,
and from this, by hydrolysis:

4-[2-(methanesulphonylamino)-ethyl]-phenoxyacetic acid m.p. 142°–143° C.;
yield 77% of theory,
sodium salt: m.p. 330° C. (decomp.).

(b) ethyl 4-[2-(p-toluenesulphonylamino)-ethyl]-phenoxyacetate m.p. 66°–67° C. (recrystallized from ethanol);
yield 74% of theory,
and from this, by hydrolysis:

4-[2-(p-toluenesulphonylamino)-ethyl]-phenoxyacetic acid m.p. 119°–120° C.; yield 93% of theory,
sodium salt as monohydrate; m.p. 245°–247° C.

(c) ethyl 4-[2-(1-naphthalenesulphonylamino)-ethyl]-phenoxyacetate m.p. 105°–106° C. (recrystallized from ethanol);
yield 65% of theory,
and from this, by hydrolysis:

4-[2-(1-naphthalenesulphonylamino)-ethyl]-phenoxyacetic acid m.p. 119°–120° C. (recrystallized from ethyl acetate+ligroin);
yield 92% of theory;
sodium salt: m.p. 238°–239° C.

(d) ethyl 4-[2-(styrenesulphonylamino)-ethyl]-phenoxyacetate m.p. 62°–63° C. (recrystallized from ethyl acetate+ligroin);
yield 71% of theory,
and from this, by hydrolysis:

4-[2-(styrenesulphonylamino)-ethyl]-phenoxyacetic acid m.p. 141°–142° C. (recrystallized from acetone+water);
yield 85% of theory.

(e) ethyl 4-[2-(4-chlorostyrenesulphonylamino)-ethyl]-phenoxyacetate m.p. 91°–92° C. (recrystallized from ethyl acetate+ligroin);
yield 76% of theory
and from this, by hydrolysis:

4-[2-(4-chlorostyrenesulphonylamino)-ethyl]-phenoxyacetic acid m.p. 147°–148° C. (recrystallized from ethyl acetate+ligroin);
yield 695 of theory.

(f) ethyl 4-[2-(4-chlorobenzenesulphonylamino)-ethyl]-phenoxyacetate m.p. 61°–62° C. (recrystallized from diethyl ether);
yield 65% of theory
and from this, by hydrolysis:

4-[2-(4-chlorobenzenesulphonylamino)-ethyl]-phenoxyacetic acid m.p. 127°–128° C. (recrystallized from acetone+water);
yield 62% of theory.

EXAMPLE 4

4-(Benzenesulphonylaminomethyl)-phenoxyacetic acid 15.7 g. (0.2 mol) Acetyl chloride are added dropwise, while cooling, to a solution of 15.9 g. (0.1 mol) 4-hydroxybenzylamine hydrochloride in 100 ml. anhydrous pyridine. The reaction mixture is subsequently stirred for 1 hour at 20° C., then heated for 15 minutes on a boiling water-bath and, while still warm, poured into ice water and acidified with concentrated hydrochloric acid. It is then extracted with chloroform and the chloroform phase is dried with anhydrous sodium sulphate and evaporated. The crude product is dissolved in ethyl acetate. After the addition of ligroin, pure 4-acetaminomethyl phenyl acetate precipitates out; yield 18.86 g. (91% of theory); m.p. 78°–79° C.

A mixture of 106.8 g. (0.515 mol) 4-acetaminomethyl phenyl acetate, 800 ml. methanol and 1030 ml. 1 N aqueous potassium hydroxide solution is heated for 2 hours at 50° C. and the methanol is distilled off in a vacuum, followed by acidification with hydrochloric acid. After concentration of the aqueous phase, the solid product is filtered off with suction and washed with ethanol. There are thus obtained 55.8 g. (66% of theory) 4-acetaminomethyl)-phenol; m.p. 132°–133° C.

A mixture of 150.0 g. (0.908 mol) 4-(acetaminomethyl)-phenol, 250.9 g. (1.816 mol) anhydrous, pulverized potassium carbonate and 3 liters butan-2-one is heated for 2 hours at reflux temperature, then cooled somewhat and 5 g. potassium iodide and 244.1 g. (1.462 mol) ethyl bromoacetate added thereto. The reaction mixture is subsequently stirred for 4 hours at reflux temperature, then cooled, filtered and the filter cake washed with acetone. The combined filtrates are evaporated in a vacuum. The evaporation residue is triturated with diethyl ether, filtered off with suction and recrystallized from isopropanol. The yield is 211.2 g. (92% of theory) ethyl 4-(acetaminomethyl)-phenoxyacetate; m.p. 93°–94° C.

A mixture of 725 ml. ethanol, 125 g. (0.5 mol) ethyl 4-(acetaminomethyl)-phenoxyacetate, 280 g. (5.0 mol) potassium hydroxide and 600 ml. water is maintained at reflux temperature for 14 hours, then cooled and adjusted to pH 4 with concentrated hydrochloric acid. The reaction mixture is filtered with suction and the filter cake is washed with water and recrystallized from aqueous ethanol. There are obtained 73.4 g. (81% of theory) 4-(aminomethyl)-phenoxyacetic acid; m.p. 260° C. (decomp.). The hydrochloride has a melting point of 252°–253° C.

While cooling in an ice-bath, dry hydrogen chloride is passed on to a mixture of 89.0 g. (0.491 mol) 4-(aminomethyl)-phenoxyacetic acid and 890 ml. anhydrous ethanol until the mixture is saturated. The reaction mixture is subsequently stirred for 12 hours at ambient temperature, a clear solution thereby being slowly formed, whereafter it is evaporated in a vacuum. There are obtained 115.3 g. (96% of theory) ethyl 4-(aminomethyl)-phenoxyacetate hydrochloride; m.p. 189°–190° C.

35.32 g. (0.2 mol) Benzenesulphonyl chloride are added dropwise, while stirring at 0° C., to a solution of 24.57 g. (0.10 mol) ethyl 4-(aminomethyl)-phenoxyacetate hydrochloride in 250 ml. anhydrous pyridine, whereafter the reaction mixture is stirred for 2 hours at ambient temperature and then poured into ice water. The aqueous phase is acidified with concentrated hydrochloric acid and then extracted with diethyl ether and chloroform. The combined extracts are washed with dilute hydrochloric acid, dried and evaporated in a vacuum. After recrystallization of the evaporation residue from isopropanol, there are obtained 30.0 g. (86% of theory) ethyl 4-(benzenesulphonylaminomethyl)-phenoxyacetate; m.p. 110°–111° C.

20.96 g. (60 mMol) Ethyl 4-(benzenesulphonylaminomethyl)-phenoxyacetate are mixed with 250 ml. methanol and 180 ml. (0.18 mol) 1 N aqueous potassium hydroxide solution. The dark red solution is stirred for 2 hours at ambient temperature and then acidified with hydrochloric acid. The methanol is now distilled off in a vacuum and cooled. The precipitated crystals are filtered off with suction, washed with water, dried and subsequently recrystallized from isopropanol. There are obtained 13.84 g. (72% of theory) 4-(benzenesulphonylaminomethyl)-phenoxyacetic acid; m.p. 142°–143° C.

In an analogous manner, by the reaction of ethyl 4-aminophenoxyacetate with the appropriate sulphonyl chloride in the presence of pyridine, there is obtained:

ethyl 4-(benzenesulphonylamino)-phenoxyacetate m.p. 127°–128° C. (recrystallized from ethyl acetate); yield 74% of theory,
and from this, by hydrolysis:

4-(benzenesulphonylamino)-phenoxyacetic acid m.p. 157°–158° C. (recrystallized from acetone+water);
yield 92% of theory.

EXAMPLE 5

2-{4-[2-(4-Chlorobenzenesulphonylamino)-ethyl]-phenoxy}-2-methylpropionic acid

A mixture of 44.8 g. (0.25 mol) N-acetyltyramine, 69.5 g. (0.5 mol) anhydrous, pulverised potassium carbonate and 750 ml. anhydrous butan-2-one is heated for 2 hours, while stirring, at reflux temperature, then 73.2 g. (0.375 mol) ethyl 2-bromo-2-methylpropionate and 1 g. potassium iodide are added thereto and the reaction mixture again heated at reflux temperature.

After 40 and 70 hours boiling, there are, in each case, additionally added 35 g. potassium carbonate and 36.6 g. ethyl 2-bromo-2-methylpropionate. After a total reaction time of 130 hours, the reaction mixture is evaporated in a vacuum, poured into ice water and extracted with diethyl ether. The ethereal extract is washed three times with 0.5 N aqueous sodium hydroxide solution and then with water and finally dried over anhydrous calcium chloride and evaporated. There are obtained 83.8 g. of an oily residue which still contains ethyl 2-bromo-2-methylpropionate. The oil is kept for 5 hours at a vacuum of 0.1 mm.Hg. and at a temperature of 70° C. The resultant crystalline slurry is washed with ligroin and dried. There are obtained 69.8 g. (95% of theory) of not quite pure ethyl 2-[4-(2-acetaminoethyl)-phenoxy]-2-methylpropionate; m.p. 51°–52° C.

A solution of 119.1 g. (0.407 mol) ethyl 2-[4-(2-acetaminoethyl)-phenoxy]-2-methylpropionate in 750 ml. ethanol is mixed with a solution of 224.4 g. (4.0 mol) potassium hydroxide in 800 ml. water and heated to reflux temperature for 8 hours. While cooling, there are added exactly 4.0 ml. hydrogen chloride (for example in the form of 2 N hydrochloric acid), cooling is intensified and, after some time, the precipitated crystals are filtered off with suction. These are washed with water and dried. The yield is 48.4 g. (53% of theory); m.p. 274° C. (decomp.).

From the mother liquor there are obtained, by distilling off the ethanol and cooling, a further 32.5 g. (36% of theory) of product; m.p. 263°–270° C. The crude 2-[4-(2-aminoethyl)-phenoxy]-2-methylpropionic acid thus obtained is recrystallized from alcohol-water (4:1 v/v) and then has a melting point of 284° C. The hydrochloride melts at 187°–189° C.

A solution of 58 g. (0.26 mol) of this carboxylic acid in 600 ml. absolute ethanol is gassed, while stirring and cooling with ice, on the surface with dry hydrogen chloride until the solution is saturated. The reaction mixture is then left to stand for 12 hours in a closed vessel. Subsequently, the ethanol and hydrogen chloride are removed in a vacuum. Water is added to the residue, followed by extracting three times with diethyl ether. The aqueous phase is rendered distinctly alkaline and extracted three times with chloroform. The chloroform extract is washed with a little water, dried over anhydrous potassium carbonate and evaporated. By distillation of the residue, there are obtained, between 125° and 128° C./0.1 mm.Hg., 53.2 g. (82% of theory) colorless ethyl 2-[4-(2-aminoethyl)-phenoxy]-2-methylpropionate. The gas chromatographically pure product has a refractive index $n_D^{20} = 1.5075$.

By the reaction of ethyl 2-[4-(2-aminoethyl)-phenoxy]-2-methylpropionate with 4-chlorobenzenesulphonyl chloride in a manner analogous to that described in Example 2, there is obtained, in a yield of 69% of theory, colorless ethyl 2-{4-[2-(4-chlorobenzenesulphonylamino)-ethyl]-phenoxy}-2-methylpropionate in the form of a viscous oil. From this there is obtained, by hydrolysis:

2-{4-[2-(4-chlorobenzenesulphonylamino)-ethyl]-phenoxy}-2-methylpropionic acid yield 67% of theory: m.p. 116° C. (recrystallized from acetone).

In an analogous manner, there is obtained:

ethyl 2-{4-[2-(benzenesulphonylamino)-ethyl]-phenoxy}-2-methylpropionate from ethyl 2-[4-(2-aminoethyl)-phenoxy]-2-methyl-propionate and benzenesulphonyl chloride;

m.p. 66°–67° C. (recrystallized from isopropanol+ligroin); yield 71% of theory;

and from this, by hydrolysis:

2-{4-[2-(benzenesulphonylamino)-ethyl]-phenoxy}-2-methylpropionic acid m.p. 128°–129° C. (recrystallized from ethyl acetate+ligroin); yield 85% of theory.

EXAMPLE 6

4-[2-(benzenesulphonylamino)-ethyl]-phenoxyacetamide.

A mixture of 67 g. (0.2 mol) 4-[2-(benzenesulphonylamino)-ethyl]-phenoxyacetic acid, 400 ml. benzene and 71.5 g. (0.6 mol) thionyl chloride is heated for 4 hours at reflux temperature. The benzene and excess thionyl chloride are then distilled off in a vacuum. The yield of crude product is quantitative. After recrystallization from methylene chloride, there are obtained 61 g. (86% of theory) 4-[2-(benzenesulphonylamino)-ethyl]-phenoxyacetyl chloride; m.p. 78.5°–79° C. With equal success, it is possible to omit the use of benzene, i.e. to use pure thionyl chloride alone.

A solution of 10.6 g. (30 mMol) 4-[2-(benzenesulphonylamino)-ethyl]-phenoxyacetyl chloride and 100 ml. anhydrous dioxan is mixed at ambient temperature with 3.3 ml. concentrated aqueous ammonia solution, then briefly warmed to 40° C. and subsequently cooled. The reaction mixture is then poured into ice water. The reaction mixture is filtered with suction and the filter cake is washed with water and digested with an aqueous solution of sodium bicarbonate. After suction filtration and washing with water, the product is recrystallized from acetone to give 7.2 g. (72% of theory) 4-[2-(benzenesulphonylamino)-ethyl]-phenoxyacetamide; m.p. 118°–119° C.

By the reaction of 4-[2-(benzenesulphonylamino)-ethyl]-phenoxyacetyl chloride with the appropriate amines, there are obtained the following amides:

(a)
4-[2-(benzenesulphonylamino)-ethyl]-phenoxyacetanilide.

3.73 g. (40 mMol) Aniline are added dropwise, with stirring, to a solution of 7.08 g. (20 mMol) acid chloride and 35 ml. anhydrous benzene. The reaction mixture is briefly warmed with 40° C. and the benzene then distilled off. Methylene chloride and dilute hydrochloric acid are added to the residue, followed by vigorous stirring, whereafter the phases are separated. The methylene chloride phase is washed with 2 N hydrochloric acid and water, dried and evaporated. After recrystallization from ethyl acetate, there are obtained 5.58 g. (68% of theory) of the desired product; m.p. 123° C.

(b)
4-[2-(Benzenesulphonylamino)-ethyl]-phenoxyacetic acid 2-ethoxycarbonylethylamide.

A mixture of 4.6 g. (30 mMol) ethyl β-aminopropionate hydrochloride, 4.1 g. (30 mMol) pulverised potassium carbonate and 100 ml. anhydrous pyridine are stirred for 20 minutes, with ice cooling, and then 10.6 g. (30 mMol) acid chloride are added dropwise thereto. The reaction mixture is subsequently allowed to warm up to 20° C., then heated for 30 minutes to 50° C., cooled and poured into about 500 ml. ice water. By the addition of hydrochloric acid, the pH is adjusted to 5.5 and the reaction mixture then extracted with methylene chloride. The methylene chloride phase is washed several times with dilute hydrochloric acid and water, dried with anhydrous sodium sulphate and evaporated. There are obtained 10.5 g. (81% of theory) of oily 4-[2-(benzenesulphonylamino)-ethyl]-propionic acid 2-ethoxycarbonylethylamide with a refractive index of $n_D^{20} = 1.5490$.

By hydrolysis thereof in a manner analogous to that described in Example 2, there is obtained:

4-[2-(benzenesulphonylamino)-ethyl]-phenoxyacetic acid 2-carboxyethylamide m.p. 64°–65° C. (recrystallized from acetone+water); yield 86% of theory.

(c) 4-[2-(benzenesulphonylamino)-ethyl]-phenoxyacetic acid 4-ethoxycarbonylanilide In a manner analogous to that described above in (b) from the acid chloride and ethyl 4-aminobenzoate hydrochloride; m.p. 157°–158° C. (recrystallized from ethyl acetate);

yield 72% of theory;

and from this, by hydrolysis:

4-[2-(benzenesulphonylamino)-ethyl]-phenoxyacetic acid 4-carboxyanilide m.p. 185°–186° C. (recrystallized from acetone+water);

yield 65% of theory;

(d) 4-[2-(benzenesulphonylamino)-ethyl]-phenoxyacetic acid 4-(ethoxycarbonylmethyleneoxy)-phenethylamide In a manner analogous to that described above in (b) from the acid chloride and ethyl 4-(2-aminoethyl)-phenoxyacetate; m.p. 97°–98° C. (recrystallized from ethyl acetate); yield 68% of theory; and from this, by hydrolysis:

4-[2-(benzenesulphonylamino)-ethyl]-phenoxyacetic acid 4-(carboxymethyleneoxy)-phenethylamide m.p. 148°–149° C. (recrystallized from water+acetone); yield 60% of theory.

EXAMPLE 7

4-[2-(n-Octanesulphonylamino)-ethyl]-phenoxyacetic acid.

26.1 g. (0.1 mol) Ethyl 4-(2-aminoethyl)-phenoxyacetate hydrochloride and 21.3 g. (0.1 mol) n-octanesulphonyl chloride are suspended in 400 ml. benzene, a solution of 27.6 g. (0.2 mol) potassium carbonate and 400 ml. water is added dropwise thereto, with very vigorous stirring, stirring is continued for 10 minutes and the phases are then separated. The benzene phase is washed with water, dried over anhydrous sodium sulphate and evaporated in a vacuum. After recrystallization of the residue from ethyl acetate, there are obtained 32.6 g. (82% of theory) ethyl 4-[2-(n-octanesulphonylamino)-ethyl]-phenoxyacetate; m.p. 65°–66° C. (after recrystallization from ethyl acetate).

A mixture of 15.4 g. (38 mMol) of this ethyl ester, 38 ml. 2 N aqueous potassium hydroxide solution and 38 ml. ethanol is kept at 40° C. for 3 hours. The ethanol is then distilled off in a vacuum and the residue is acidified with hydrochloric acid, filtered with suction and the product thus obtained recrystallized from a water-dioxan mixture. There are obtained 12.4 g. (88% of theory) 4-[2-(n-octanesulphonylamino)-ethyl]-phenoxyacetic acid; m.p. 128°–129° C.

EXAMPLE 8

4-[2-(n-Hexadecanesulphonylamino)-ethyl]-phenoxyacetic acid.

5.5 g. (16.9 mMol) n-Hexadecanesulphonyl chloride are added at 0° C., with vigorous stirring, to a mixture of 4.4 g. (16.9 mMol) ethyl 4-(2-aminoethyl)-phenoxyacetate hydrochloride, 50 ml. benzene and 6.8 g. (68 mMol) triethylamine. The reaction mixture is stirred for a further 2 hours in an ice-bath and then left to stand overnight at 20° C. The reaction mixture is then poured on to ice water, acidified with hydrochloric acid and extracted with diethyl ether. The ethereal phase is washed with water, dried with anhydrous sodium sulphate, evaporated and the residue recrystallized from ethanol to give 5.8 g. (67% of theory) ethyl 4-[2-(n-hexadecanesulphonylamino)-ethyl]-phenoxyacetate; m.p. 91°–92° C.

Hydrolysis of the ester is carried out analogously to Example 7 with aqueous potassium hydroxide solution in methanol. There is obtained a yield of 68% of theory of 4-[2-(n-hexadecanesulphonylamino)-ethyl]-phenoxyacetic acid; m.p. 137.5°–138° C. (recrystallized from ethanol).

EXAMPLE 9

In a manner analogous to that described in Example 3, by the reaction of ethyl 4-(2-aminoethyl)-phenoxyacetate hydrochloride with the appropriate sulphonyl chloride in the presence of pyridine, there are obtained the following compounds:

(a) ethyl 4-[2-(2-phenylethanesulphonylamino)-ethyl]-phenoxyacetate as a viscous oil (crude product); yield 76% of theory, and from this, by hydrolysis:

4[2-(2-phenylethanesulphonylamino)-ethyl]-phenoxyacetic acid m.p. 124°–125° C. (recrystallized from ethanol+10% water); yield 74% of theory.

(b) ethyl 4-{2-[2-(4-chlorophenyl)-ethanesulphonylamino]-ethyl}-phenoxyacetate as a viscous oil (crude product); yield 57% of theory; and from this, by hydrolysis:

4-{2-[2-(4-chlorophenyl)-ethanesulphonylamino]-ethyl}-phenoxyacetic acid m.p. 128°–130° C. (recrystallized from ethyl acetate+ligroin); yield 73% of theory.

(c) Ethyl-4-[2-(4-acetylbenzenesulphonylamino)-ethyl]-phenoxyacetate m.p. 113.5°–114° C. (recrystallized from ethyl acetate+ligroin); yield 52% of theory and from this, by hydrolysis:

4-[2-(4-acetylbenzenesulphonylamino)-ethyl]-phenoxyacetic acid m.p. 162° C. (recrystallized from acetone); yield 63% of theory.

EXAMPLE 10

4-[2-(Benzenesulphonylamino)-ethyl]-phenoxyacetic acid 1-hydroxy-2-propylamide.

A solution of 6.4 g. (18 mMol) 4-[2-(benzenesulphonylamino)-ethyl]-phenoxyacetyl chloride and 25 ml. anhydrous benzene is added dropwise at 0° to 5° C., over the course of 2 hours, to a mixture of 5.4 g. (72 mMol) 1-hydroxy-2-aminopropane and 35 ml. water, a precipitate thereby forming slowly. After standing overnight at 20° C., the precipitate is filtered off with suction and the filter cake is washed with dilute aqueous sodium hydroxide solution and then with water and dried. After recrystallization from ethyl acetate, there are obtained 5.2 g. (74% of theory) of the desired product; m.p. 90°–91° C.

EXAMPLE 11

4-[2-(N-Methylbenzenesulphonylamino)-ethyl]-phenoxyacetic acid.

0.6 g. (25 mMol) Sodium hydride (suspension in mineral oil) are added to a mixture of 9.1 g. (25 mMol) ethyl 4-[2-(benzenesulphonylamino)-ethyl]-phenoxyacetate, 50 ml. hexamethylphosphoric acid triamide and 50 ml. anhydrous toluene and the reaction mixture subsequently stirred for 2 hours at 80° C. The reaction mixture is then cooled, mixed with a mixture of 10.6 g. (75 mMol) methyl iodide and 10 ml. hexamethylphosphoric acid triamide, stirred for 15 minutes at 20° C. and then kept for 3 hours at 80° C. After cooling, the reaction mixture is poured on to ice water, adjusted to pH 3 by means of hydrochloric acid and extracted several times with toluene. The toluene phase is evaporated and the evaporation residue chromatographed on silica gel with the use of toluene. There are obtained 3.9 g. (41% of theory) pure ethyl 4-[2-(N-methylbenzenesulphonylamino)-ethyl]-phenoxyacetate in the form of a colorless oil with the refractive index $n_D^{20} = 1.5440$.

This compound can also be obtained in the following manner:

9.25 g. (54 mMol) Benzenesulphonic acid monomethylamide are dissolved in 75 ml. hexamethylphosphoric acid triamide, 1.3 g. (54 mMol) sodium hydride (in the form of a mineral oil suspension) is added thereto, the reaction mixture is stirred for 20 minutes at 20° C. and then 14.9 g. (54 mMol) ethyl 4-(2-bromoethyl)-phenoxyacetate are added thereto. The reaction mixture is stirred for 24 hours at 50° C., cooled and poured into ice water. The pH is adjusted to 3 by means of dilute hydrochloric acid and extracted several times with toluene. The toluene phase is washed with water and dried with anhydrous sodium sulphate. The product is then chromatographed on silica gel with toluene to give 9.2 g. (45% of theory) of the desired ester.

From this there is obtained, by hydrolysis with 1 N aqueous potassium hydroxide in ethanol, 4-[2-(N-methylbenzenesulphonylamino)-ethyl]-phenoxyacetic acid; m.p. 103°–104° C. (recrystallized from ethyl acetate+ligroin); yield 91% of theory.

EXAMPLE 12

4-[3-(Benzenesulphonylamino)-propyl]-phenoxyacetic acid.

A mixture of 14.5 g. (75 mMol) 4-(3-acetaminopropyl)-phenol, 16.8 g. (122.5 mMol) pulverized potassium carbonate and 150 ml. butan-2-one is maintained at reflux temperature for 2 hours, then 20.6 g. (122.5 mMol) ethyl bromoacetate and a spatula tip of potassium iodide are added thereto and the reaction mixture maintained at 80° C. for 6 hours. The reaction mixture is then filtered with suction and the filtrate evaporated in a vacuum and, for the separation of excess ethyl bromoacetate, finally at oil pump vacuum. The evaporation residue is taken up in methylene chloride and extracted with cold 0.5 N aqueous sodium hydroxide solution and then with water. After drying with anhydrous sodium sulphate, the solution is evaporated and, by cooling and adding diethyl ether, crystallization is brought about. After recrystallization from diethyl ether, there are obtained 14.9 g. (71% of theory) ethyl 4-(3-acetaminopropyl)-phenoxyacetate; m.p. 57°–58° C.

A mixture of 16.2 g. (58 mMol) ethyl 4-(3-acetaminopropyl)-phenoxyacetate, 100 ml. ethanol, 100 ml. water and 32.5 g. (0.58 mol) potassium hydroxide is kept at reflux temperature for 16 hours. The reaction mixture is then cooled, adjusted to pH 6.5 with 6 N hydrochloric acid and the resultant sand-colored precipitate filtered off with suction. After washing with water and drying, there are obtained 12.0 g. (quantitative yield) 4-(3-aminopropyl)-phenoxyacetic acid; m.p. 248° C.

A mixture of 9.7 g. (46.5 mMol) 4-(3-aminopropyl)-phenoxyacetic acid, 6.9 g. (50 mMol) potassium carbonate and 100 ml. water is heated to 80° C. and 8.5 g. (48 mMol) benzenesulphochloride added dropwise thereto at this temperature. Thereafter, the reaction mixture is kept at 80° C. for a further 2 hours, then cooled and adjusted to pH 2 with 2 N hydrochloric acid. The precipitate obtained is filtered off with suction, dried and crystallised from ethyl acetate and then from glacial acetic acid to give 8.26 g. (51% of theory) 4-[3-(benzenesulphonylamino)-propyl]-phenoxyacetic acid; m.p. 146°–147° C.

EXAMPLE 13

2-{4-[2-(Benzenesulphonylamino)-ethyl]-phenoxy}-2-methylpropionic acid. (using the chloroform-acetone method)

9.4 g. (235 mMol) Sodium hydroxide are added to a mixture of 4.45 g. (16.1 mMol) 4-[2-(benzenesulphonylamino)-ethyl]-phenol and 77 ml. acetone at 20° C., while stirring. Within 2 hours, 8.7 g. (72.9 mMol) chloroform are added dropwise, whereby, by occasional cooling, the internal temperature is kept at 30° to 35° C. The reaction mixture is then further stirred for 30 minutes at 30° C. and then heated at reflux temperature for 2.5 hours. The reaction mixture is then evaporated in a vacuum and the residue is taken up in water and extracted with diethyl ether. The aqueous phase is acidified and extracted with ethyl acetate. The ethyl acetate phase is dried with anhydrous sodium sulphate and evaporated in a vacuum. The residue is mixed with 50 ml. water and 5 g. sodium bicarbonate and stirred, a clear solution thereby being obtained. This is again extracted with diethyl ether. The aqueous phase is now acidified and extracted with ethyl acetate. After evaporation of the ethyl acetate, the residue is recrystallized from an ethyl acetate-ligroin mixture, with the addition of charcoal, to give 2.64 g. (45% of theory) of the desired acid which, in all physical properties, is identical with the product obtained in Example 5.

EXAMPLE 14

2-[4-(4-Chlorobenzenesulphonylamino)-phenoxy]-2-methylpropionic acid.

A mixture of 139.1 g. (1 mol) 4-nitrophenol, 1 liter butan-2-one and 207.3 (1.5 mol) pulverized, anhydrous potassium carbonate is stirred for 2 hours at reflux temperature, then 292.5 g. (1.5 mol) ethyl 2-bromo-2-methylpropionate are added thereto and the reaction mixture maintained at reflux temperature for a further 92 hours. After the addition of a further 69.1 g. (0.5 mol) potassium carbonate and 97.5 g. (0.5 mol) ethyl 2-bromo-2-methyl-propionate, the reaction mixture is stirred for a further 20 hours at reflux temperature. The reaction mixture is then filtered with suction and the filtrate is evaporated in a vacuum (for the removal of excess ethyl ester, finally at a high vacuum). The residue is taken up in diethyl ether, filtered and the ethereal phase now extracted several times with 1 N aqueous sodium hydroxide solution. After washing until neutral and drying, it is evaporated, 153 g. (60% of theory) of an oily crude product being obtained. After distillation at 155.5°–156° C./0.05 mm.Hg., there is obtained a yield of 46% of theory of pure ethyl 2-methyl-2-(4-nitrophenoxy)-propionate in the form of a yellow oil with a refractive index of $n_D^{20} = 1.5288$.

A mixture of 50.6 g. (0.2 mol) ethyl 2-methyl-2-(4-nitrophenoxy)-propionate, 500 ml. ethanol and about 20 g. 5% palladium charcoal is hydrogenated in a shaker at ambient temperature and atmospheric pressure until the necessary amount of hydrogen has been taken up. The reaction mixture is subsequently filtered with suction and the liquid phase is evaporated to give a quantitative yield of crude ethyl 2-(4-aminophenoxy)-2-methylpropionate in the form of a distillable oil (b.p. 134°–135° C./0.05 mm.Hg.); $n_D^{20} = 1.5035$; m.p. of the hydrochloride 153°–154° C.

10.6 g. (50 mMol) 4-Chlorobenzenesulphochloride are added within the course of 30 minutes at 0°–5° C. to a mixture of 13.0 g. (50 mMol) ethyl 2-(4-aminophenoxy)-2-methylpropionate hydrochloride and 200 ml. anhydrous pyridine. The reaction mixture is then stirred for 1 hour at 5° C. and finally maintained for 2 hours at 80° C. The reaction mixture is then cooled, stirred into ice water and acidified with hydrochloric acid to pH 5.5, an oily product thereby separating out. This is taken up in diethyl ether. The ethereal phase is successively washed with 6 N hydrochloric acid, water, aqueous sodium bicarbonate solution and again with water, dried and evaporated in a vacuum. There are obtained 18.8 g. (95% of theory) crude ethyl 2-[4-(4-chlorobenzenesulphonylamino)-phenoxy]-2-methyl-propionate in the form of a colorless oil. By saponification of the crude ester by means of 1 N aqueous potassium hydroxide solution in ethanol in a manner analogous to that described in Example 2, there is obtained a yield of 91% of theory of crystalline 2-[4-(4-chlorobenzenesulphonylamino)-phenoxy]-2-methylpropionate; m.p. 146.5°–147° C. (after recrystallization from ethyl acetate+ligroin).

The following compounds are obtained in an analogous manner:

(a) ethyl 2-[4-(4-chlorostyrenesulphonylamino)-phenoxy]-2-methylpropionate.

From p-chlorostyrenesulphonyl chloride and ethyl 2-(4-aminophenoxy)-2-methylpropionate;
m.p. 130°–131° C. (recrystallized from ethyl acetate); yield 87% of theory,
and from this, by hydrolysis:

2-[4-(4-chlorostyrenesulphonylamino)-phenoxy]-2-methylpropionic acid m.p. 172°–173° C. (recrystallized from ethyl acetate); yield 73% of theory.

(b) ethyl 2-{4-[2-(4-chlorostyrenesulphonylamino)-ethyl]-phenoxy}-2-methylpropionate From p-chlorostyrenesulphonyl chloride and ethyl 2-[4-(2-aminoethyl)-phenoxy]-2-methylpropionate; colourless oil, $n_D^{20} = 1.5625$;
and from this, by hydrolysis:

2-{4-[2-(4-chlorostyrenesulphonylamino)-ethyl]-phenoxy}-2-methylpropionic acid m.p. 148°–149° C. (recrystallized from benzene); yield 76% of theory.

(c) ethyl 2-{4-{2-[2-(4-chlorophenyl)-ethanesulphonylamino]-ethyl}-phenoxy}-2-methylpropionate from 2-(4-chlorophenyl)-ethanesulphonyl chloride and ethyl 2-[4-(2-aminoethyl)-phenoxy]-2-methylpropionate; colorless oil; yield 77% of theory, and from this, by hydrolysis:

2-{4-{2-[2-(4-chlorophenyl)-ethanesulphonylamino]-ethyl}-phenoxy-}-2-methylpropionic acid m.p. 138°–139° C. (recrystallized from ethyl acetate+ligroin); yield 53% of theory.

EXAMPLE 15

2-{4-[2-(4-Chlorobenzenesulphonylamino)-ethyl]-phenoxy}-n-hexanoic acid.

A mixture of 17.92 g. (0.1 mol) 4-(2-acetamino-ethyl)-phenol, 17.3 g. (0.125 mol) pulverized potassium carbonate and 150 ml. butan-2-one is stirred for 2 hours at reflux temperature, then 27.9 g. (0.125 mol) ethyl 2-bromohexanoate and a spatula tip of potassium iodide are added thereto and the reaction mixture kept at reflux temperature for a further 28 hours. The reaction mixture is then filtered with suction and the filtrate evaporated in a vacuum. The residue is taken up in diethyl ether and the ethereal phase is extracted with 2 N hydrochloric acid, water, 0.5 N aqueous sodium hydroxide solution and again with water, dried over anhydrous sodium sulphate and evaporated to give 32.1 g. (quantitative yield) ethyl 2-[4-(2-acetaminoethyl)-phenoxy]-n-hexanoate in the form of a colorless oil with a refractive index $n_D^{20} = 1.5010$.

A mixture of 25.7 g. (80 mMol) ethyl 2-[4-(2-acetaminoethyl)-phenoxy]-n-hexanoate, 150 ml. water, 150 ml. ethanol and 44.9 g. (0.8 mol) potassium hydroxide is kept at reflux temperature for 16 hours and the alcohol subsequently distilled off in a vacuum. After the addition of 150 ml. water, the reaction mixture is acidified to pH 4 with hydrochloric acid and the resultant precipitate is filtered off with suction, washed with water and dried. There are obtained 12.5 g. (62% of theory) 2-[4-(2-aminoethyl)-phenoxy]-n-hexanoic acid; m.p. 274°–276° C.

By the reaction of 2-[4-(2-aminoethyl)-phenoxy]-n-hexanoic acid with 4-chlorobenzenesulphonyl chloride in the presence of aqueous potassium carbonate solution, in a manner analogous to that described in Example 1, there is obtained a yield of 32% of theory of 2-{4-[2-(4-chlorobenzenesulphonylamino)-ethyl]-phenoxy}-n-hexanoic acid; m.p. 138°–139° C. (recrystallized from ethyl acetate and cyclohexane).

The activity of the instant compounds in inhibiting thrombocyte aggregation is demonstrated by the following illustrative experiments:

In a series of determinations utilizing the Born test, venous blood from metabolically healthy persons was mixed with sodium citrate in a ratio of 9:1 and the erythrocytes precipitated by centrifuging at 150 g. The filtrate is enriched in thrombocytes and this filtrate is designated as platelet-rich plasma (PRP). One aliquot of the PRP is placed in the cuvette of an aggregometer (Universal Aggregometer, manufactured by Braun Melsungen, West Germany) and stirred with a magnetic stirrer. The substance to be tested is added in the form of an aqueous solution at a pH of about 7. Changes in the light transmission of the suspension are continuously recorded. After spontaneous aggregation ceases, further aggregation is induced by the addition of $5 \times 10^{-6}$ m adrenalin, forming larger thrombocyte aggregates and increasing the light transmission through the suspension.

The adrenalin induced aggregation takes place in two phases, i.e., the light transmission initially increases, then stagnates temporarily, and then increases again. Only the second phase of the aggregation can be influenced by aggregation inhibitors. For an evaluation of the results there is first established, in a control experiment using no test compound, the angle of the second aggregation phase against the horizontal for adrenalin induced aggregation and this is designated as 0% inhibition. Utilizing the same PRP, the test compound is added and aggregation is induced with adrenalin, and the course of aggregation continuously recorded. The angle of the second aggregation phase against the horizontal is again determined and the relationship of this angle against the angle determined in the control experiment yields the percent inhibition of the second phase of the thrombocyte aggregation.

The standard material "Colfarit" (acetylsalicylic acid) yields 100% inhibition at a concentration of $10^{-4}$ m and 0% inhibition at a concentration of $5 \times 10^{-5}$ m. At the latter concentration the inventive compounds yielded the following results:

| Test Compound | Percent Inhibition Of Thrombocyte Aggregation (at $5 \times 10^{-5}$m) |
|---|---|
| 4-[2-(benzolsulfonylamino-ethyl]-phenoxyacetic acid | 100% |
| 4-[2-(benzolsulfonylamino)-ethyl]phenoxyacetic acid-isopropyl ester | 100% |
| 4-[2-(4-fluorobenzolsulfonylamino)-ethyl]-phenoxyacetic acid | 100% |
| 4-[2-(p-toluolsulfonylamino)-ethyl]-phenoxyacetic acid | 100% |
| 4-[2-(1-naphthalenesulfonylamino)-ethyl]-phenoxyacetic acid | 100% |
| 4-[2-(4-chlorobenzolsulfonylamino)-ethyl]-phenoxyacetic acid | 100% |
| 4-(benzolsulfonylamino-methyl)-phenoxyacetic acid | 20% |
| 2-{4-[2-(4-chlorobenzolsulfonylamino)-ethyl]-phenoxy}-2-methyl-propionic acid | 100% |

| Test Compound | Percent Inhibition Of Thrombocyte Aggregation (at 5 × 10⁻⁵m) |
|---|---|
| 2-{4-[2-(benzolsulfonylamino)-ethyl]-phenoxy}-2-methyl propionic acid | 20% |
| 4-[2-(benzolsulfonylamino)-ethyl]-phenoxyacetic acid-(2-ethoxycarbonyl-ethylamide) | 100% |
| 4-[2-(4-acetylbenzolsulfonylamino)-ethyl]-phenoxyacetic acid | 100% |
| 4-[2-(benzolsulfonylamino)-ethyl]-phenoxyacetic acid-(1-hydroxy-2-propylamide) | 10% |
| 4[3-(benzolsulfonylamino)-propyl]-phenoxyacetic acid | 100% |

The above table shows that the inventive compounds are far superior to the standard comparison substance, acetylsalicylic acid, in that the inventive compounds demonstrate a substantial and often 100% inhibition at a concentration where the comparison substance yields 0% inhibition.

The novel compounds may be administered by themselves or in conjuction with carriers which are pharmacologically acceptable, either active or inert. The dosage units are similar to those of the heretofore known thrombocyte aggregation inhibitors, e.g., 2 to 3 grams per day for thrombo-phlebitis or 1 to 1.5 grams per day for venous thromboses, although higher and lower dosages can be used, e.g., the dosage should be lowered after the acute symptoms of thrombo-phlebitis have moderated. Rather than adminstering a single dosage, it is preferable that the compounds are dosed evenly over the course of the day, e.g., in applications of 0.5 to 1 g, three times a day.

For the preparation of pharmaceutical compositions, at least one of the new compounds is mixed with a solid or liquid pharmaceutical carrier or diluent and optionally with an odoriferous, flavoring and/or coloring material and formed, for example, into tablets or dragees, or with the addition of appropriate adjuvants, suspended or dissolved in water or in an oil, for example, olive oil.

The compounds can be administered orally or parenterally in liquid or solid form. As injection medium, it is preferred to use water which contains the stabilizing agents, solubilizing agents and/or buffers, conventional for injection solutions. Additives of this type include, for example, tartrate and borate buffers, ethanol, dimethyl sulphoxide, complex-forming agents (such as ethylene diaminetetraacetic acid), high molecular weight polymers (such as liquid polyethylene oxide) for viscosity regulation or polyoxyethylene derivatives of sorbitan anhydrides.

Solid carrier materials include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and sweetening agents. For topical application, the compounds according to the present invention can also be employed in the form of powders and salves. For this purpose, they are mixed with, for example, powdered, physiologically compatible diluents or with conventional salve bases.

It will be appreciated that the instant specification and examples are set forth by way of illustration and not limitation, and that various modifications and changes may be made without departing from the spirit and scope of the present invention.

What is claimed is:

1. Phenoxyalkylcarboxylic acid compound of the formula

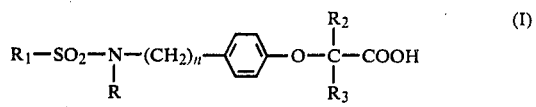

wherein

R is hydrogen or lower alkyl of up to 6 carbon atoms $R_1$ is aryl, aralkyl or aralkenyl wherein the aryl moiety contains from 6 to 14 carbon atoms, and the alkyl or alkenyl moiety contains up to 5 carbon atoms and wherein said aralkyl and aralkenyl is optionally substituted with at least one substituent selected from halogen, hydroxyl, trifluoromethyl, alkyl or alkoxy of up to 5 carbon atoms, and alkanoyl of up to 5 carbon atoms $R_2$ and $R_3$ are individually selected from hydrogen or lower alkyl of up to 6 carbon atoms, and n is 0, 1, 2 or 3 or the physiologically acceptable salt or lower alkyl ester thereof.

2. Phenoxyalkylcarboxylic acid compound as claimed in claim 1 wherein R is hydrogen.

3. Phenoxyalkylcarboxylic acid compound as claimed in claim 1 wherein $R_1$ is aryl, aralkyl or aralkenyl wherein the aryl moiety contains from 6 to 14 carbon atoms, and the alkyl or alkenyl moiety contains up to 5 carbon atoms.

4. Phenoxyalkylcarboxylic acid compound as claimed in claim 1 wherein $R_1$ is substituted aryl, aralkyl or aralkenyl wherein the substituent is on the aryl moiety and is selected from halogen, hydroxyl, trifluoromethyl, alkyl or alkoxy of up to 5 carbon atoms and alkanoyl of up to 5 carbon atoms.

5. Phenoxyalkylcarboxylic acid compound as claimed in claim 1 wherein one of $R_2$ and $R_3$ is hydrogen.

6. Phenoxyalkylcarboxylic acid compound as claimed in claim 1 wherein one of $R_2$ and $R_3$ is alkyl of up to 6 carbon atoms.

7. Phenoxyalkylcarboxylic acid compound as claimed in claim 1 wherein both of $R_2$ and $R_3$ are hydrogen.

8. Phenoxyalkylcarboxylic acid compound as claimed in claim 1 wherein both of $R_2$ and $R_3$ are alkyl of up to 6 carbon atoms.

9. Phenoxyalkylcarboxylic acid compound as claimed in claim 1 wherein n is 0.

10. Phenoxyalkylcarboxylic acid compound as claimed in claim 1 wherein n is 1.

11. Phenoxyalkylcarboxylic acid compound as claimed in claim 1 wherein n is 2.

12. Phenoxyalkylcarboxylic acid compound as claimed in claim 1 wherein n is 3.

13. Phenoxyalkylcarboxylic acid compound as claimed in claim 1 designated 4-[2-(phenylsulfonylamino)-ethyl]-phenoxyacetic acid.

14. Phenoxyalkylcarboxylic acid compound as claimed in claim 1 designated 4-[2-(phenylsulfonylamino)-ethyl]-phenoxyacetic acid-isopropyl ester.

15. Phenoxyalkylcarboxylic acid compound as claimed in claim 1 designated 4-[2-(4-fluorophenylsulfonylamino)-ethyl]-phenoxyacetic acid.

16. Phenoxyalkylcarboxylic acid compound as claimed in claim 1 designated 4-[2-(1-naphthalenesulfonylamino)-ethyl]-phenoxyacetic acid.

17. Phenoxyalkylcarboxylic acid compound as claimed in claim 1 designated 4-[3-(phenylsulfonylamino)-propyl]-phenoxyacetic acid.

18. Composition for inhibiting thrombocyte aggregation which composition comprises a pharmacologically acceptable carrier and, in effective amounts, a phenoxyalkylcarboxylic acid compound as claimed in claim 1.

19. Method for inhibiting thrombocyte aggregation in an afflicted host which method comprises administering to such host effective amounts of a phenoxyalkylcarboxylic acid compound as claimed in claim 1.

20. Method as claimed in 19 wherein said phenoxyalkylcarboxylic acid compound is selected from
- 4-[2-(phenylsulfonylamino)-ethyl]-phenoxyacetic acid
- 4-[2-(phenylsulfonylamino)-ethyl]-phenoxyacetic acid-isopropyl ester
- 4-[2-(4-fluorophenylsulfonylamino)-ethyl]-phenoxyacetic acid
- 4-[2-(1-naphthalenesulfonylamino)-ethyl]-phenoxyacetic acid
- 4-[2-phenylsulfonylamino)-ethyl]-phenoxyacetic acid-(2-ethoxycarbonylethylamide), and
- 4-[3-(phenylsulfonylamino)-propyl]-phenoxyacetic acid.

* * * * *